(12) United States Patent
Chen et al.

(10) Patent No.: US 11,883,418 B2
(45) Date of Patent: Jan. 30, 2024

(54) COMPOUND TSYI-ZAC FOR INHIBITING DENGUE VIRUS INFECTION AND MEDICINAL USE THEREOF

(71) Applicant: Syi Biotechnology Co., Ltd., Taichung (TW)

(72) Inventors: Chia-Chang Chen, Taichung (TW); Guey-Chuen Perng, Tainan (TW); Hsiu-Man Lien, Taichung (TW); Yi-Ju Chen, Taichung (TW)

(73) Assignee: SYI BIOTECHNOLOGY CO., LTD., Taichung (TW)

( * ) Notice: Subject to any disclaimer, the term of this patent is extended or adjusted under 35 U.S.C. 154(b) by 0 days.

(21) Appl. No.: 17/835,221

(22) Filed: Jun. 8, 2022

(65) Prior Publication Data

US 2023/0285415 A1   Sep. 14, 2023

(30) Foreign Application Priority Data

Mar. 9, 2022  (TW) .................................. 111108474

(51) Int. Cl.
*A61K 31/575* (2006.01)
*A61K 31/357* (2006.01)
*A61P 31/20* (2006.01)

(52) U.S. Cl.
CPC .......... *A61K 31/575* (2013.01); *A61K 31/357* (2013.01); *A61P 31/20* (2018.01)

(58) Field of Classification Search
CPC ....... A61K 31/575; A61P 31/20; A61P 31/357
See application file for complete search history.

(56) References Cited

U.S. PATENT DOCUMENTS

2020/0268771 A1\*   8/2020   Wu ........................ A61P 31/22

\* cited by examiner

*Primary Examiner* — Timothy R Rozof
(74) *Attorney, Agent, or Firm* — Muncy, Geissler, Olds & Lowe, P.C.

(57) ABSTRACT

A compound TSYI-ZAC (Zhankuic acid C) used in a method for treating dengue virus infection, in which a pharmaceutical composition can further comprise a 4,7-dimethoxy-5-methyl-1,3-benzodioxole compound capable of inhibiting dengue virus infection by down-regulating an expression of IL-6 and IL-8, and increasing a secretion of IFN-α.

8 Claims, 4 Drawing Sheets

COMPOUND TSYI-ZAC FOR INHIBITING DENGUE VIRUS INFECTION AND MEDICINAL USE THEREOF

BACKGROUND OF THE INVENTION

Field of Invention

The invention relates to a use of a compound TSYI-ZAC for inhibiting dengue virus infection, and more particularly to a use of inhibiting dengue virus infection by down-regulating an expression of IL-6 and IL-8 and increasing a secretion of IFN-α.

Related Art

Dengue virus is a positive-stranded RNA virus, which belongs to the yellow fever virus of the genus Flavivirus. Dengue patients have a wide range of symptoms, ranging from asymptomatic patients, mild fever, bone pain, etc., dengue in a small number of patients may develop into severe dengue, such as dengue hemorrhagic fever (DHF) and dengue shock syndrome (DSS). However, most of the current treatments for dengue use supportive therapy, and there is no effective drug or vaccine against dengue virus directly.

*Antrodia camphorata* (*Antrodia cinnamomea*) is a parasitic fungus with a plate-like appearance and a dark red surface, which is often used for health care, because *Antrodia camphorata* only parasitically grows on the *Cinnamomum kanehirae*, a broad-leafed evergreen megaphanerophyte tree that grows at high altitudes, *Antrodia camphorata* is also known as "*Antrodia* mushroom" or "Taiwanofungus camphoratus". *Antrodia camphorata* is rich in triterpenoids, polysaccharides (such as β-D-glucan), adenosine, vitamins (e.g., vitamin B, niacin), proteins (including immunoglobulins), etc., has efficacies of anti-cancer, anti-allergy, antipruritic, and treating diarrhea, and subsequently found that *Antrodia camphorata* also has a good therapeutic effect on chronic diseases such as diabetes and hypertension. Further, there are documents pointing out that the polysaccharides of *Antrodia camphorata* have an effect of inhibiting hepatitis B virus. Whether the *Antrodia camphorata* extract can be used as a drug for the treatment of dengue fever is not well understood.

Some dengue patients have plasma leakage during fever, which can increase the risk of developing into severe dengue. One of the main reasons is believed to be that dengue virus alters the expression of inflammation-related factors, causing endothelial cell damage in patients. Both IL-6 and IL-8 are considered to be major cytokines that are capable of regulating endothelial cell permeability; while TNF-α is considered to be a main cytokine that is capable of triggering cell apoptosis mechanism of dengue virus infection. There are documents pointing out that dengue virus can help dengue virus infection and replication by reducing the antiviral mechanism of type 1 IFN (IFN-α, IFN-β) in patients; however, there is currently no document pointing out that compounds (such as compound TSYI-ZAC) in *Antrodia camphorata* extract can inhibit dengue virus infection, let alone there is previous document related to inhibition of dengue virus infection by using compound TSYI-ZAC with 4,7-dimethoxy-5-methyl-1,3-benzodioxole compound.

SUMMARY OF THE INVENTION

In view of the above, the inventor of the invention has a deep understanding of the deficiencies and drawbacks in the prior art, and is eager to improve and innovate. After years of research, the inventor has successfully developed a compound TSYI-ZAC for inhibiting dengue virus infection and a medicinal use thereof.

In order to achieve the above object, the invention provides a method for treating dengue virus infection with a compound TSYI-ZAC, wherein the compound TSYI-ZAC is a Zhankuic acid C compound.

In one embodiment of the invention, treating dengue virus infection with the compound TSYI-ZAC and a 4,7-dimethoxy-5-methyl-1,3-benzodioxole compound as a pharmaceutical composition.

In one embodiment of the invention, the compound TSYI-ZAC is capable of inhibiting an expression of IL-6.

In one embodiment of the invention, the compound TSYI-ZAC is capable of inhibiting an expression of IL-8.

In one embodiment of the invention, the compound TSYI-ZAC is capable of increasing a secretion of IFN-α.

In one embodiment of the invention, a dose of the compound TSYI-ZAC is 5 μg/mL to 100 μg/mL.

In one embodiment of the invention, a dose of the compound TSYI-ZAC is 25 μg/mL to 91.68 μg/mL.

In one embodiment of the invention, a dose of the 4,7-dimethoxy-5-methyl-1,3-benzodioxole compound is 5 μg/mL to 200 μg/mL.

In one embodiment of the invention, a dose of the 4,7-dimethoxy-5-methyl-1,3-benzodioxole compound is 25 μg/mL to 176.51 μg/mL.

The invention further provides a method for inhibiting dengue virus infection with a compound TSYI-ZAC, by contacting cells with the compound TSYI-ZAC to inhibit the cells from being infected by the dengue virus, wherein the compound TSYI-ZAC is a Zhankuic acid C compound.

BRIEF DESCRIPTION OF THE DRAWINGS

The techniques of invention would be more understandable from the detailed description given herein below and the accompanying figures are provided for better illustration, and thus description and figures are not limitative for invention, and wherein.

DETAILED DESCRIPTION OF THE INVENTION

Definition of Terms

Figure 1:
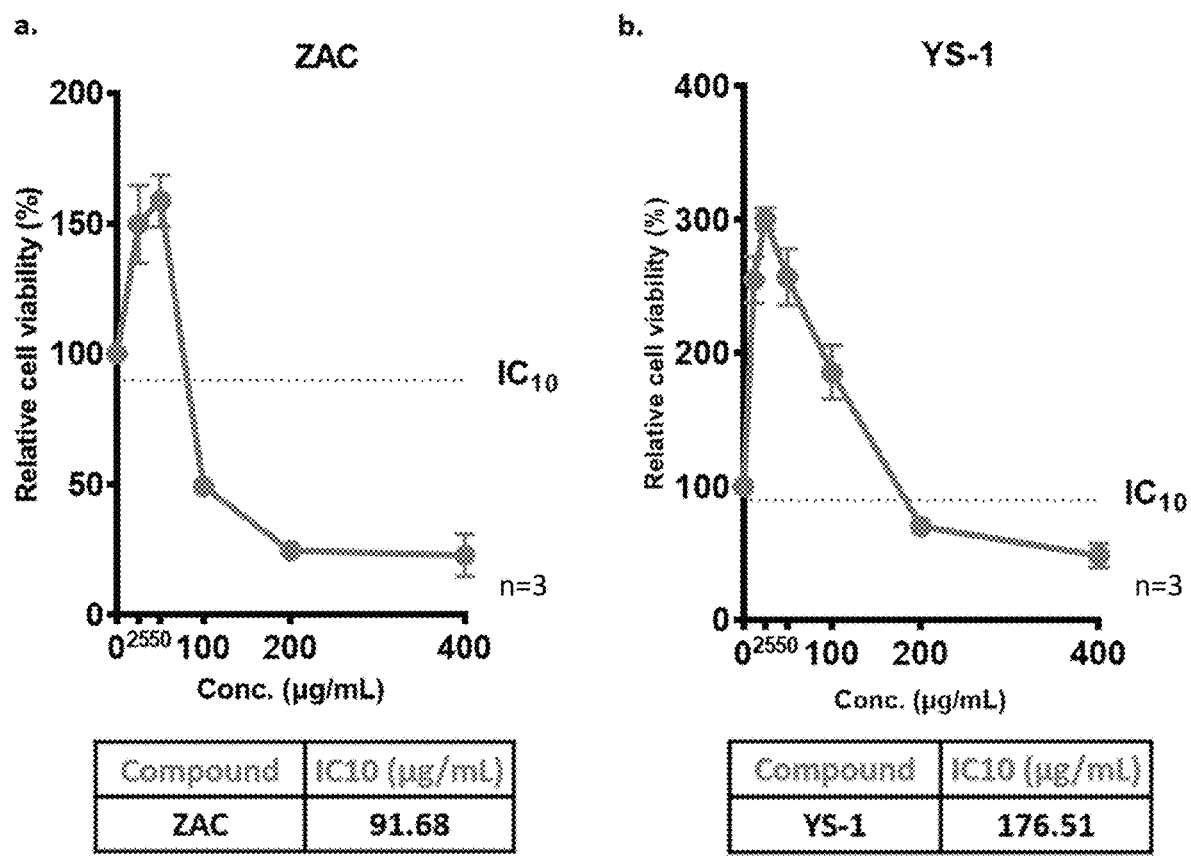
FIG. 1 is a graph of viability of Meg-01 cells after adding an *Antrodia camphorata* extract according to one embodiment of the invention, wherein a of FIG. 1 is a viability curve (n=3) of the Meg-01 cells after adding an *Antrodia camphorata* extract ZAC, b of FIG. 1 is a viability curve (n=3) of the Meg-01 cells after adding an *Antrodia camphorata* extract YS-1.

Many common technical and scientific terms in the field of biotechnology are used extensively in this specification, in the following description, the following definitions are provided for a clear and consistent understanding of the scope of this specification and the claims to which these terms are characterized. Other terms that are not specifically defined below have the meanings commonly understood in the field of professionals involved.

The terms "individual", "patient" and similar terms are used herein to refer to a mammal undergoing treatment evaluation stage and/or being treated. In one embodiment, the mammal is a human. Thus, the term "patient" encompasses individuals infected with dengue virus. An individual can be a human, and includes other mammals, such as mouse, rat, etc., which are particularly suitable for using as laboratory models of human diseases.

The term "pharmaceutical composition" refers to a solid or liquid composition in a form, concentration and degree of purity suitable for administration to a patient, in which after administration is capable of inducing desired physiological changes; a pharmaceutical composition is sterile and/or non-pyrogenic.

The term "treatment" and similar terms used herein mean to administer a certain medicament in order to obtain a certain effect. The effect is partial or complete therapeutically effective cure of a certain disease and/or symptoms of the disease. As used herein, "treatment" encompasses any treatment of dengue virus infection in mammals (particularly human), and includes: (a) inhibition of disease, i.e., prevention of its development; and (b) alleviation of disease, i.e., regression of disease.

The terms "therapeutically effective amount", "therapeutic dose" and similar terms used herein mean a medicament amount or dose that is effective in treating, curing, preventing or ameliorating a disease, disorder, or side effect, or reducing a rate of progression of a disease or disorder. The term also includes an amount or a dose within its limit capable of effectively enhancing normal physiological functions.

The term "pharmaceutically acceptable" means that a substance or a composition must be compatible with other ingredients in its pharmaceutical formulation and does not exacerbate a patient's symptoms.

A pharmaceutical composition provided by the invention is prepared in a dosage form suitable for use in the invention, in which an effective ingredient or composition provided in the invention and at least one pharmaceutically acceptable vehicle are used in techniques well known to a person having ordinary in the art to which the invention pertains. Wherein the dosage form includes, but is not limited to, solution, emulsion, suspension, powder, tablet, lozenge, troche, chewing gum, capsule and other similar dosage forms suitable for the invention.

The term "pharmaceutically acceptable vehicle" includes one ingredient form or more than one ingredient form selected from the following: solvent, emulsifier, suspending agent, decomposing agent, binder, excipient, stabilizer, chelating agent, diluent, gellant, preservative, lubricant, surfactant, and other similar vehicles suitable for the invention.

In the aforementioned composition, one of or more than one of dissolution adjuvant, buffer, coloring agent, flavoring agent commonly used in the field of preparation of medication can also be appropriately added as needed.

The term "pharmaceutically acceptable excipient" includes, but is not limited to, at least one of polymer, resin, plasticizer, filler, lubricant, diluent, binder, disintegrant, solvent, co-solvent, surfactant, preservative, sweetener, flavoring agent, pharmaceutical grade dye or pigment, and viscosity agent.

The term "cell culture" and similar terms are used herein to maintain cells in an artificial in vitro environment. However it should be understood that the term "cell culture" is a generic term and can be used to cover not only the cultivation of individual cells, but also the cultivation of tissues or organs.

The term "multiplicity of infection (MOI)" herein refers to the ratio of infectious agents to infection targets, its calculation formula is: multiplicity of infection=number of viral particles/number of host cells.

The term "plaque forming unit (PFU)" herein refers to a number of viruses that form one viral plaque (phage) on cells cultured in monolayer, which is used as a unit for quantifying viral content.

The term "plaque viral titer" herein refers to an amount of viruses contained in one milliliter of a culture medium, its calculation formula is: viral titer (PFU/ml)=(plaque unit)*1000/400*(dilution factor).

[Dengue Virus]

The serotype of dengue virus infection that can be inhibited by an *Antrodia camphorata* extract of the invention is not particularly limited, as an embodiment, the following can be enumerated: dengue virus type 1 (DENV-1), dengue virus type 2 (DENV-2), dengue virus type 3 (DENV-3), dengue virus type 4 (DENV-4), dengue virus type 5 (DENV-5), or a derived virus of the above.

Compound TSYI-ZAC and
4,7-dimethoxy-5-methyl-1,3-benzodioxole
Compound

A source of a compound TSYI-ZAC and a 4,7-dimethoxy-5-methyl-1,3-benzodioxazole compound (abbreviated as YS-1, molecular weight 196.07) of the invention is not limited, which can be extracted from *Antrodia camphorata*, or can be purchased commercially, wherein the compound TSYI-ZAC is a Zhankuic acid C (abbreviated as ZAC, molecular weight 486.64) compound; in one embodiment of the invention, the compound TSYI-ZAC and the 4,7-dimethoxy-5-methyl-1,3-benzodioxole compound are extracted from *Antrodia camphorata*, which are referred to as an *Antrodia camphorata* extract ZAC and an *Antrodia camphorata* extract YS-1 respectively hereinafter.

[Method for Treating Dengue Virus Infection]

The invention discloses a method for treating dengue virus infection. The method is about administering a therapeutically effective amount of *Antrodia camphorata* extract to a patient in need, preferably administering a therapeutically effective amount of the *Antrodia camphorata* extract ZAC or the *Antrodia camphorata* extract YS-1, more preferably administering a therapeutically effective amount of the *Antrodia camphorata* extract ZAC and the *Antrodia camphorata* extract YS-1.

The method of the invention relates to administration of the *Antrodia camphorata* extract ZAC and/or the *Antrodia camphorata* extract YS-1 to an individual (e.g., a human patient) to inhibit dengue virus infection. A treatment method in accordance with the method of the invention can also treat, cure, mitigate, alleviate, alter, remedy, ameliorate, enhance or affect a disease, symptoms or conditions of the disease, disability caused by the disease, or a progression of the disease.

[Administration of the *Antrodia camphorata* Extract ZAC and the *Antrodia camphorata* Extract YS-1]

The pharmaceutical composition of the invention can be delivered by any physiologically acceptable route, and can be administered locally or systemically, with or without addition of excipients, such as oral, parenteral (e.g., intramuscular, intravenous, subcutaneous, and intraperitoneal), transdermal, suppository, and intranasal methods. For parenteral administration, it is preferably used in the form of a sterile aqueous solution, which can contain other substances sufficient to make the solution isotonic with blood, such as salt or dextrose. The aqueous solution (preferably pH 3 to 9) can be appropriately buffered as needed. Preparation of a suitable parenteral composition under sterile conditions can be accomplished by standard pharmacological techniques known to those skilled in the art.

[Dose]

In the treatment method of the invention, an effective amount of the *Antrodia camphorata* extract ZAC and/or the *Antrodia camphorata* extract YS-1 is administered to an individual in need; in detail, the effective amount varies depending on an object of administration, health and physical conditions and age of an individual to be treated, the taxonomic group of an individual to be treated (e.g., human, non-human primate, primate, etc.), dosage form of the *Antrodia camphorata* extract ZAC and/or the *Antrodia camphorata* extract YS-1, clinician's assessment of medical situation, and other relevant factors. It is expected that the amount will be within a relatively wide range, which can be determined via routine experimentation. For example, in order to fully inhibit dengue virus infection, a dose of the *Antrodia camphorata* extract ZAC is preferably 5 μg/mL to 100 μg/mL, more preferably 25 μg/mL to 91.68 μg/mL, and a dose of the *Antrodia camphorata* extract YS-1 is preferably 5 μg/mL to 200 μg/mL, more preferably 25 μg/mL to 176.51 μg/mL.

[Pharmaceutical Composition]

The *Antrodia camphorata* extract ZAC and/or the *Antrodia camphorata* extract YS-1 can be mixed with a pharmaceutically acceptable carrier (for example, in the form of a pharmaceutically acceptable salt) to prepare the pharmaceutical composition; and can also be packaged in a container, and prepared as a reagent kit or product together with a package insert containing information related to *Antrodia camphorata* extract and usage.

The invention is exemplified and illustrated by the following embodiments; however, the following embodiments are purely exemplifications of the invention, so they should not be regarded as limitations of the scope of the invention in any way, in addition, materials used below are all readily available commercially.

[Preparation of *Antrodia camphorata* Extract]

Both the compound TSYI-ZAC and the 4,7-dimethoxy-5-methyl-1,3-benzodioxole compound of the invention are extracted from *Antrodia camphorata* to prepare the *Antrodia camphorata* extract ZAC and the *Antrodia camphorata* extract YS-1 respectively, and re-lysed with dimethyl sulfoxide (DMSO) and prepared into *Antrodia camphorata* extract with different concentrations.

[Cell Culture]

Meg-01 cell strains (CRL2021, ATCC, human myelomegakaryocyte leukemia cell strains) are cultured in a RPMI medium with 10% fetal bovine serum, when a cell density reaches 80-90%, the cell sap can be withdrawn into a centrifuge tube, after being centrifuged in a centrifuge (600 rpm, 6 minutes), then remove the supernatant, and re-lyse the centrifuged cells with an appropriate amount of a culture medium for subculture or subsequent experiments.

[Cell Viability Assay]

$1 \times 10^3$ Meg-01 cells are lysed in 100 μL of 10% fetal bovine serum in a RPMI culture medium and seeded into a 96-well U-shaped plate. Different concentrations of the *Antrodia camphorata* extract ZAC and the *Antrodia camphorata* extract YS-1 are added to the cells for co-culture at 37° C. for 7 days, while the cells added with dimethyl sulfoxide (DMSO) are used as an experimental control group. After 7 days, WST-1 Assay Reagent (Roche, USA) is added for cytotoxicity test, and OD 440 nm value is collected to calculate a cell survival rate and a concentration of drug $IC_{10}$ (ZAC $IC_{10}$: 91.675 μg/mL, YS-1 $IC_{10}$: 176.512 μg/mL) for subsequent drug assay experiments.

[Dengue Virus Infection (DENV Infection)]

$2 \times 10^4$ Meg-01 cells are lysed in a RPMI culture medium containing 10% fetal bovine serum for in vitro infection with dengue virus. The infection condition is 1 MOI, a total volume of virus sap and cell sap is 2 ml, and the selected virus is dengue virus type 2 (DENV-2), strain 16681. The infection mixture is cultured in a 37° C. incubator for 2 hours, and the tube is shaken once every 30 minutes to increase a chance of virus contacting the cells. After 2 hours, centrifuge (600 rpm, 6 minutes) with a centrifuge to remove the virus that is not in contact with the cells, and re-lyse the cells with an appropriate amount of a cell culture medium, and then divide the cells into a cell culture medium (2 ml) or into a cell culture medium additional added with the *Antrodia camphorata* extract ZAC and the *Antrodia cam-*

*phorata* extract YS-1, the centrifuge tube is finally placed in a 37° C. incubator, and the infection supernatant is collected at specific infection time points (time points: 2 hours, and 1, 2, 3, 5, 7 days after infection). The infection mixture is taken out at the specific time points, centrifuged with a centrifuge (600 rpm, 6 minutes), the infection supernatant is separated, and a viral titer is assayed by viral plaque assay and an expression of cytokines is assayed by enzyme combined with immunosorbent assay.

[Plaque Assay]

$7\times10^5$/well mouse kidney epithelial cells (BHK cells) are lysed in 1.5 ml of a DMEM culture medium containing 5% fetal bovine serum and seeded on a 6-well plate. The virus solution to be tested will be serially diluted first. The preparation method is to add 100 μL of unknown virus solution to 900 μL of a DMEM culture medium containing 2% fetal bovine serum to achieve a 10-fold dilution. After the cells to be seeded are attached onto the plate, remove the culture medium, add 400 μL of the virus solution to be tested, and culture in a 37° C. incubator for 2 hours. The plate needs to be shaken once every 15 minutes so that the infection solution can evenly cover the cells. After two hours, the infection solution is removed, methylcellulose is added to limit a range of virus movement, and the plate is placed back into the 37° C. incubator to culture for 7 days. After 7 days, the six-well plate is taken out, and each well is washed with PBS, and then stained with crystal violet for 1 hour (cells can be stained, no cells or dead cells will not be stained). Finally, the dye is washed off with clean water, and a number of plaques formed is counted to calculate the viral titer. Calculation formula: viral titer (PFU/ml)=(plaque unit)*1000/400*(dilution factor).

Embodiment 1

Please refer to FIG. 1. FIG. 1 is a graph of viability of Meg-01 cells after adding the *Antrodia camphorata* extract according to one embodiment of the invention. The Meg-01 cells are co-cultured with different concentrations of the *Antrodia camphorata* extract ZAC or the *Antrodia camphorata* extract YS-1 respectively, and the group added with DMSO is used as an experimental control group. After the cells are co-cultured with the *Antrodia camphorata* extract for 7 days, WST-1 assay reagent is added to the cells and OD 440 nm value is collected to assay a toxicity of the drug on the cells, the cell group without addition of the *Antrodia camphorata* extract is regarded as an experimental control group, and the cell groups added with different concentrations of the *Antrodia camphorata* extract are regarded as experimental groups. Calculation method of cell viability: experimental group/control group×100%; from the cell viability graph in a of FIG. 1, it can be seen that the *Antrodia camphorata* extract ZAC with low concentrations (25 μg/mL, 50 μg/mL) generally has no toxicity on the Meg-01 cells, while higher concentrations of the *Antrodia camphorata* extract ZAC (100 μg/mL, 200 μg/mL, 400 μg/mL) have a slight effect on cell viability; it can be seen from the cell viability curve in b of FIG. 1 that low concentrations of the *Antrodia camphorata* extract YS-1 (25 μg/mL, 50 μg/mL, 100 μg/mL) are generally not toxic to the Meg-01 cells, while higher concentrations of the *Antrodia camphorata* extract YS-1 (200 μg/mL, 400 μg/mL) have a slight effect on cell viability.

Then, $IC_{10}$ of the *Antrodia camphorata* extract ZAC and the *Antrodia camphorata* extract YS-1 (concentration that produces 10% inhibition of cell viability) are calculated by two-way ANOVA analysis, and the results are 91.68 μg/mL and 176.51 μg/mL respectively, so in subsequent experiments, if not specifically mentioned, the above $IC_{10}$ concentrations are used as doses of the *Antrodia camphorata* extract added in experiments.

Embodiment 2

Figure 2:
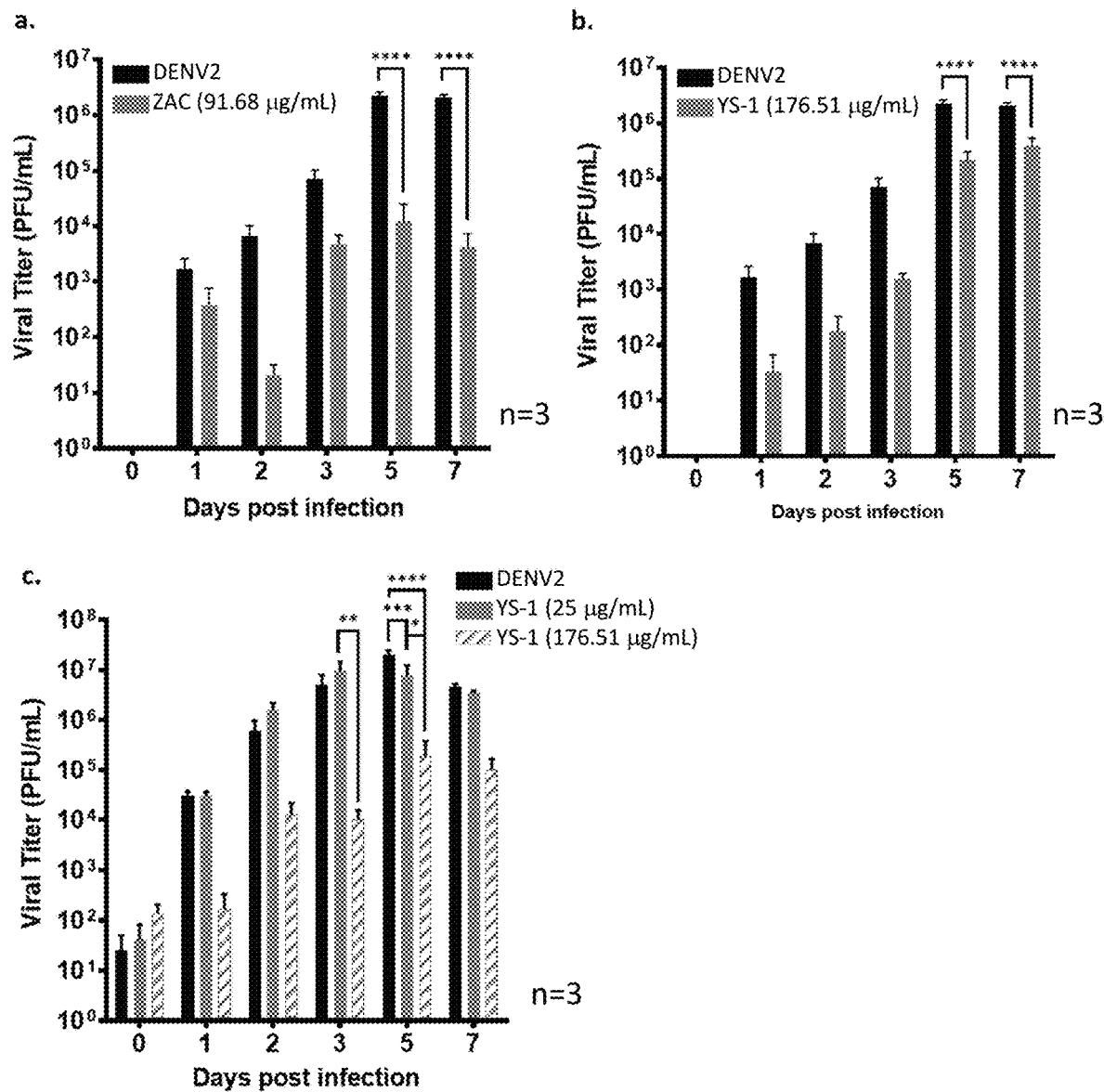
FIG. 2 shows that the Meg-01 cells added with the *Antrodia camphorata* extract are capable of effectively inhibiting dengue virus infection according to one embodiment of the invention, wherein a of FIG. 2 is a dengue viral titer (n=3) produced by adding the *Antrodia camphorata* extract ZAC (91.68 μg/mL) after the Meg-01 cells are infected by dengue virus; b of FIG. 2 is a dengue viral titer (n=3) produced by adding the *Antrodia camphorata* extract YS-1 (176.51 μg/mL) after the Meg-01 cells are infected by dengue virus; and c of FIG. 2 is a dengue viral titer (n=3) produced by adding the *Antrodia camphorata* extract YS-1 with different concentrations (25 μg/mL, 176.51 μg/mL) after the Meg-01 cells are infected by dengue virus.

In order to assay an effect of the *Antrodia camphorata* extract on dengue virus infection, please refer to FIG. 2, FIG. 2 shows that the Meg-01 cells added with the *Antrodia camphorata* extract are capable of effectively inhibiting dengue virus infection according to one embodiment of the invention. 2 hours after the Meg-01-01 cells are infected by dengue virus, centrifuge to remove excessive virus, and the cells are re-lysed in a cell culture medium containing the *Antrodia camphorata* extract ZAC (91.68 μg/mL) or the *Antrodia camphorata* extract YS-1 (176.51 μg/mL), respectively. The cells not infected with dengue virus and the cells without adding the *Antrodia camphorata* extract after infected with dengue virus (marked as DENV2 in the figure) are used as experimental control groups. The infected supernatant is collected 2 hours, 1, 2, 3, 5, and 7 days after infection. Plaque assay will be used on the collected infected supernatant (n=3) to quantify a viral titer. It can be seen from a of FIG. 2 that, in the part where the *Antrodia camphorata* extract ZAC is added, compared with the experimental control groups, after the Meg-01-01 cells are infected by dengue virus, an overall viral titer of the group added with the *Antrodia camphorata* extract ZAC tends to decrease, especially in the late stages of infection (5th to 7th days), the dengue viral titer of the group added with the *Antrodia camphorata* extract ZAC decreases significantly (with statistical difference, ****, p value<0.0001). It can be seen from b of FIG. 2 that, in the part where the *Antrodia camphorata* extract YS-1 is added, the results are the same as above, adding the *Antrodia camphorata* extract YS-1 after infection is capable of significantly reducing the viral titer (with statistical difference, ****, p value<0.0001); in order to assay whether different concentrations have a difference in inhibiting dengue virus infection, different concentrations of the *Antrodia camphorata* extract YS-1 are added, it can be seen from c of FIG. 2 that no matter whether the *Antrodia camphorata* extract YS-1 is high dose (176.51 μg/mL) or low dose (25 μg/mL), it has an inhibitory effect on dengue virus, wherein adding a high dose of the *Antrodia camphorata* extract YS-1 has better inhibitory effect on dengue virus.

It can be known from the above results that both the *Antrodia camphorata* extract ZAC and the *Antrodia camphorata* extract YS-1 are capable of effectively reducing the viral titer and inhibiting the infection of dengue virus, and the inhibitory effect enhances with an increase of a dose concentration of the *Antrodia camphorata* extract.

Embodiment 3

Figure 3:
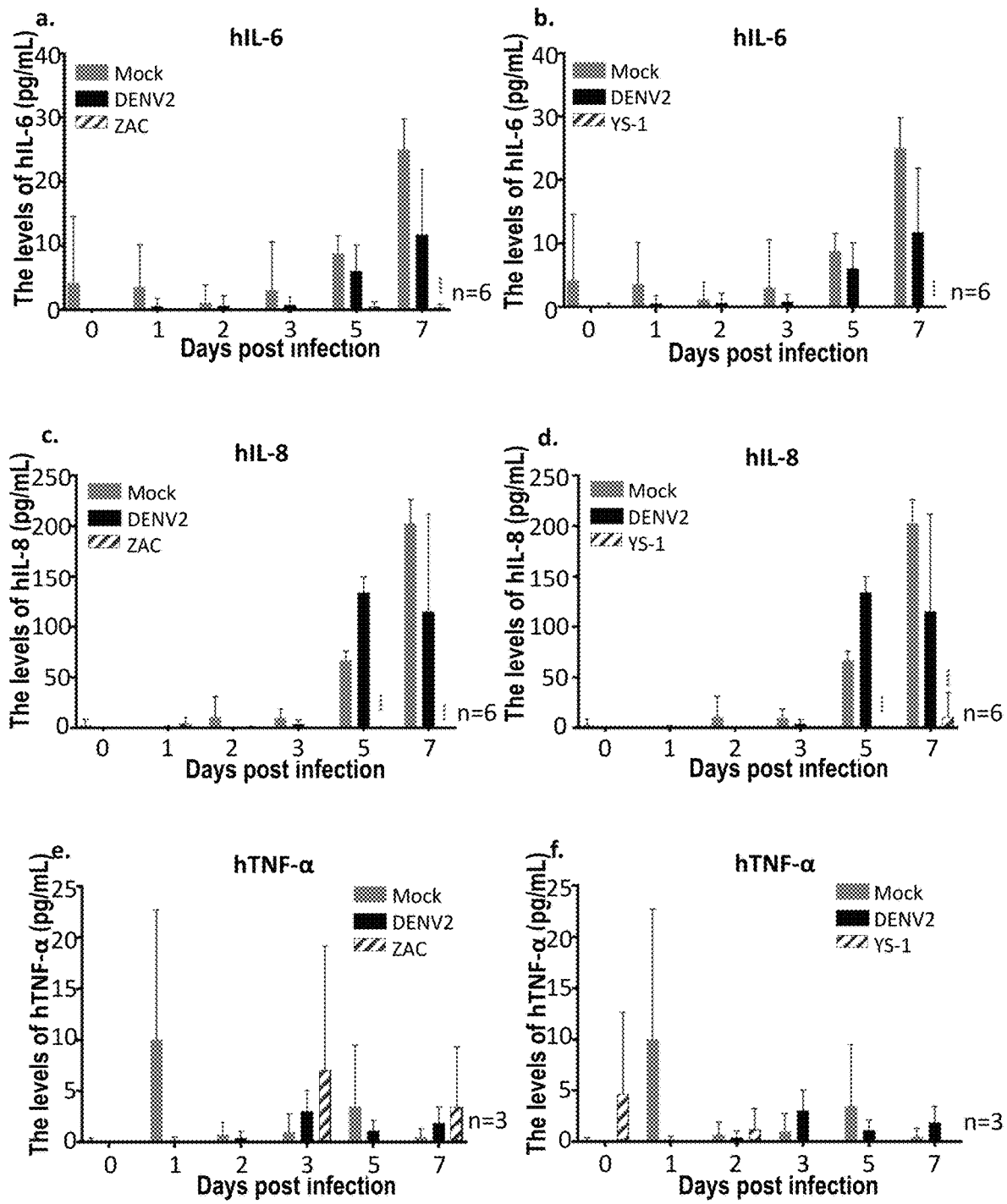
FIG. 3 shows that addition of the *Antrodia camphorata* extract is capable of effectively down-regulating an expression of cellular inflammatory factors IL-6 and IL-8 after dengue virus infection of the Meg-01 cells according to one embodiment of the invention, wherein blue color represents addition of the *Antrodia camphorata* extract ZAC, red color represents addition of the *Antrodia camphorata* extract YS-1, black color represents no addition of the *Antrodia camphorata* extract but infected with dengue virus, gray color represents blank control (mock), a of FIG. 3 is an expression level of cellular inflammatory factor IL-6 in the Meg-01 cells added with the *Antrodia camphorata* extract ZAC; b of FIG. 3 is an expression level of cellular inflammatory factor IL-6 in the Meg-01 cells added with the *Antrodia camphorata* extract YS-1; c of FIG. 3 is an expression level of cellular inflammatory factor IL-8 in the Meg-01 cells added with the *Antrodia camphorata* extract ZAC; d of FIG. 3 is an expression level of cellular inflammatory factor IL-8 in the Meg-01 cells added with the *Antrodia camphorata* extract YS-1; e of FIG. 3 is an expression level of cellular inflammatory factor TNF-α in the Meg-01 cells added with the *Antrodia camphorata* extract ZAC; and f of FIG. 3 is an expression level of cellular inflammatory factor TNF-α in the Meg-01 cells added with the *Antrodia camphorata* extract YS-1.

In order to confirm an expression of cellular inflammatory factors (IL-6, IL-8, TNF-α) in the collected infected supernatant, the infected supernatant is assayed by enzyme immunoassay. Please refer to FIG. 3, where blue color represents addition of the *Antrodia camphorata* extract ZAC, red color represents addition of the *Antrodia camphorata* extract YS-1, black color represents no addition of the *Antrodia camphorata* extract but infected with dengue virus (marked as DENV2 in the figure), gray color represents blank control (marked as Mock in the figure). It can be known from the results that after dengue virus infection, whether adding the

*Antrodia camphorata* extract ZAC or the *Antrodia camphorata* extract YS-1 is capable of effectively reducing an expression of cellular inflammatory factors, especially effectively reducing an expression of cellular inflammatory factors cellular IL-6, IL-8.

It can be known from the above results that both the *Antrodia camphorata* extract ZAC and the *Antrodia camphorata* extract YS-1 are capable of inhibiting a inflammatory response, thereby inhibiting the infection of dengue virus.

Embodiment 4

Figure 4:
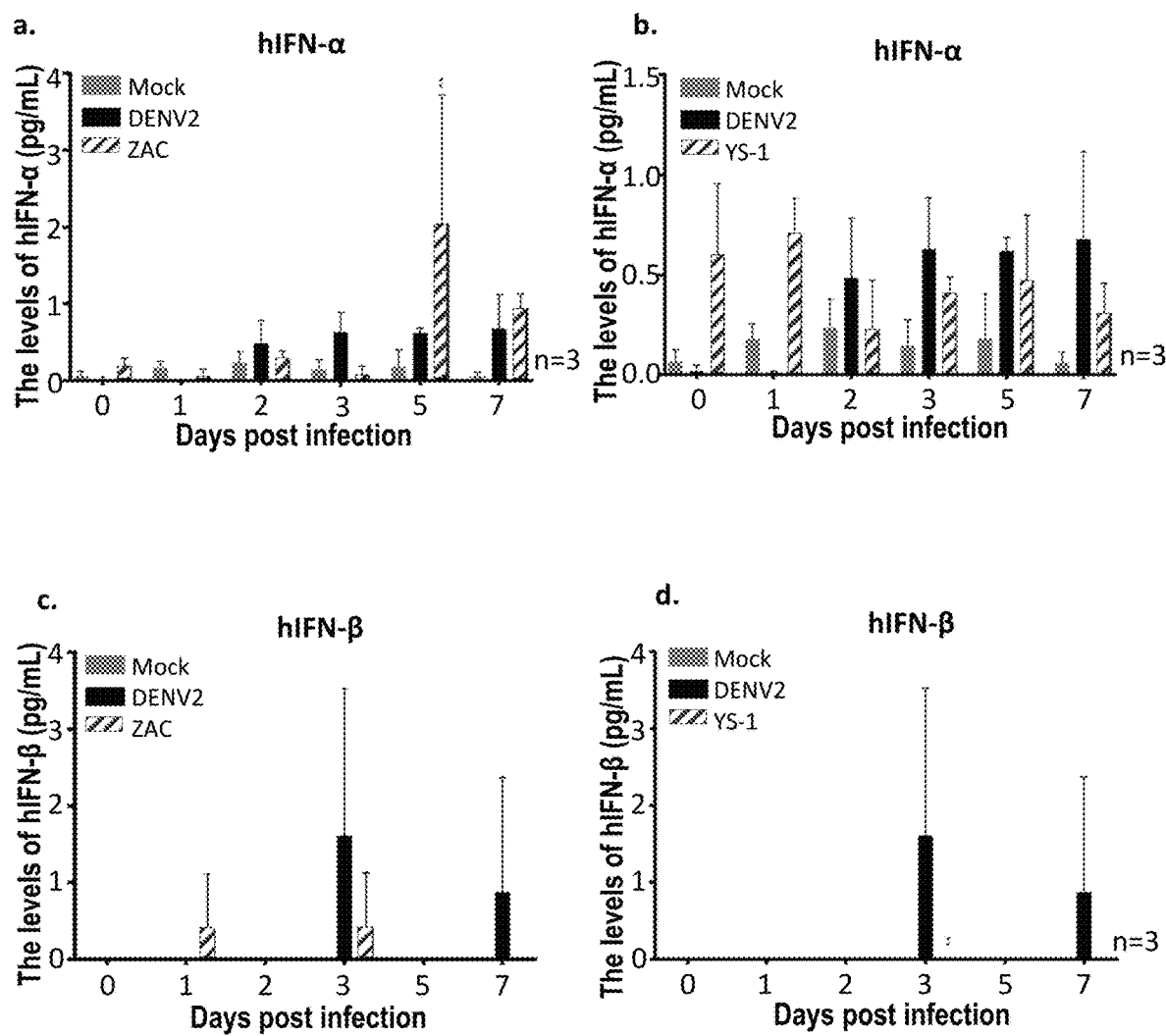
FIG. 4 shows that the *Antrodia camphorata* extract ZAC is capable of inhibiting dengue virus infection by increasing a secretion of IFN-α to enhance an antiviral ability of the cells according to one embodiment of the invention, wherein a of FIG. 4 is an expression level of cellular antiviral factor IFN-α in the Meg-01 cells added with the *Antrodia camphorata* extract ZAC; b of FIG. 4 is an expression level of cellular antiviral factor IFN-α in the Meg-01 cells added with the *Antrodia camphorata* extract YS-1; c of FIG. 4 is an expression level of cellular antiviral factor IFN-β in the Meg-01 cells added with the *Antrodia camphorata* extract ZAC; and d of FIG. 4 is an expression level of cellular antiviral factor IFN-β in the Meg-01 cells added with the *Antrodia camphorata* extract YS-1.

In order to confirm an expression of antiviral factors (IFN-α, IFN-β) in the collected infected supernatant, the infected supernatant is assayed by enzyme immunoassay. Please refer to FIG. 4, where blue color represents addition of the *Antrodia camphorata* extract ZAC, red color represents addition of the *Antrodia camphorata* extract YS-1, black color represents no addition of the *Antrodia camphorata* extract but infected with dengue virus (marked as DENV2 in the figure), gray color represents blank control (marked as Mock in the figure). It can be known from the results that after dengue virus infection, the group with addition of the *Antrodia camphorata* extract ZAC is capable of effectively increasing an expression of antiviral factor IFN-α in the cells in the late stages of dengue virus infection, so as to enhance an antiviral ability of the cells, especially on the 5th and 7th days after infection, an amount of secretion of IFN-α in the cells is significantly higher than that of the experimental control group (after infected with dengue virus, the cells are lysed in a culture medium without adding the *Antrodia camphorata* extract), wherein on the 5th day after infection, there is a significant difference in IFN-α between the group with addition of the *Antrodia camphorata* extract ZAC and the experimental control group (statistically significant, **P value is 0.0021).

It can be known from the above results that the *Antrodia camphorata* extract ZAC is capable of effectively increasing an expression of IFN-α in the cells, thereby inhibiting the infection of dengue virus.

In summary, after adding the compound TSYI-ZAC and the 4,7-dimethoxy-5-methyl-1,3-benzodioxole compound, almost all the expressions of the cellular inflammation-related factors (IL-6, IL-8) are low. Especially after dengue virus infection of the Meg-01 cells, addition of the compound TSYI-ZAC is capable of effectively increasing a secretion of antiviral factor IFN-α by the cells, thereby achieving a function of inhibiting dengue virus infection.

The above-mentioned embodiments are merely used to illustrate the technical ideas and features of the invention, with an object to enable any person having ordinary skill in the art to understand the technical content of the invention and implement it accordingly, the embodiments are not intended to limit the claims of the invention, and all other equivalent changes and modifications completed based on the technical means disclosed in the invention should be included in the claims covered by the invention.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for treating dengue virus infection, comprising administrating an effective amount of a pharmaceutical composition comprising compound TSYI-ZAC and 4,7-dimethoxy-5-methyl-1,3-benzodioxole to a subject in need of, wherein the compound TSYI-ZAC is a Zhankuic acid C compound, a dose of the compound TSYI-ZAC is 5 μg/mL to 100 μg/mL, and a dose of 4,7-dimethoxy-5-methyl-1,3-benzodioxole compound is 5 μg/mL to 200 μg/mL.

2. The method as claimed in claim 1, wherein the compound TSYI-ZAC is capable of inhibiting an expression of IL-6.

3. The method as claimed in claim 1, wherein the compound TSYI-ZAC is capable of inhibiting an expression of IL-8.

4. The method as claimed in claim 1, wherein the compound TSYI-ZAC is capable of increasing a secretion of IFN-α.

5. The method as claimed in claim 1, wherein the dose of the compound TSYI-ZAC is 25 μg/mL to 91.68 μg/mL.

6. The method as claimed in claim 1, wherein a dose of 4,7-dimethoxy-5-methyl-1,3-benzodioxole is 5 μg/mL to 200 μg/mL.

7. The method as claimed in claim 1, wherein a dose of 4,7-dimethoxy-5-methyl-1,3-benzodioxole is 25 μg/mL to 176.51 μg/mL.

8. A method for inhibiting dengue virus infection with a compound TSYI-ZAC, comprising contacting cells with the compound TSYI-ZAC to inhibit cells being infected by the dengue virus, wherein the compound TSYI-ZAC is a Zhankuic acid C compound, and a dose of the compound TSYI-ZAC is 5 μg/mL to 100 μg/mL.

* * * * *